US006801594B1

(12) United States Patent
Ali et al.

(10) Patent No.: US 6,801,594 B1
(45) Date of Patent: Oct. 5, 2004

(54) COMPUTED TOMOGRAPHY FLUOROSCOPY SYSTEM

(75) Inventors: Fazle Ali, Brookfield, WI (US); Jiang Hsieh, Brookfield, WI (US); Robert F. Senzig, Germantown, WI (US); Steven C. Davis, Brookfield, WI (US); Shawn P. Faessler, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 1111 days.

(21) Appl. No.: 08/979,279

(22) Filed: Nov. 26, 1997

(51) Int. Cl.$^7$ ............................................... G01N 23/00
(52) U.S. Cl. .......................................... 378/4; 378/114
(58) Field of Search ............................. 378/4, 114, 115

(56) References Cited

U.S. PATENT DOCUMENTS 4,773,086 A * 9/1988 Fujita et al. ................. 378/116
4,807,273 A    2/1989 Haendle
5,220,592 A    6/1993 Blouir
5,440,606 A    8/1995 Faul et al.

* cited by examiner

Primary Examiner—Craig E. Church
(74) Attorney, Agent, or Firm—Carl B. Horton, Esq.; Armstrong Teasdale LLP

(57) ABSTRACT

A CT Fluoro system which, in one embodiment, includes an integrated controller, image reconstruction algorithms for increasing the speed of image display, and an enhanced image display, is described. The integrated controller enables the radiologist to maintain control of the system throughout the fluoro scan. The image reconstruction algorithms are generally directed to increasing the image frame rate or reducing image artifacts, or both, in the CT fluoro scan. The image display generally provides enhanced images and control to the radiologist during a scan procedure.

21 Claims, 7 Drawing Sheets

COMPUTED TOMOGRAPHY FLUOROSCOPY SYSTEM

FIELD OF THE INVENTION

This invention relates generally to computed tomography (CT) imaging and more particularly, to a CT fluoroscopic system.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array: of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsffield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

In CT fluoroscopic systems ("CT Fluoro"), data collected from a helical scan may be utilized to generate sequential frames of images to help, for example, in guiding a needle to a desired location within a patient. A frame, like a view, corresponds to a two dimensional slice taken through the imaged object. Particularly, projection data is processed at a frame rate to construct an image frame of the object.

With known CT Fluoro systems, the general objective is to increase the frame rate while minimizing image degradation. Increasing the frame rate provides many advantages including, for example, that an operator physician is provided with increased information regarding the location of a biopsy needle. Typically, however, increasing the frame rate is at odds with minimizing image degradation. In addition, it is desirable to provide an operator with control of the scanning process as well as the display of images for guiding the procedure.

SUMMARY OF THE INVENTION

These and other objects may be attained by a CT Fluoro system which, in one embodiment, includes an integrated controller, image reconstruction algorithms for increasing the speed of image display, and an enhanced image display. The integrated controller enables the radiologist to maintain control of the system throughout the fluoro scan. The image reconstruction algorithms are generally directed to increasing the image frame rate or reducing image artifacts, or both, in the CT fluoro scan. The image display generally provides enhanced images and control to the radiologist during a scan procedure.

DETAILED DESCRIPTION

Figure 1:
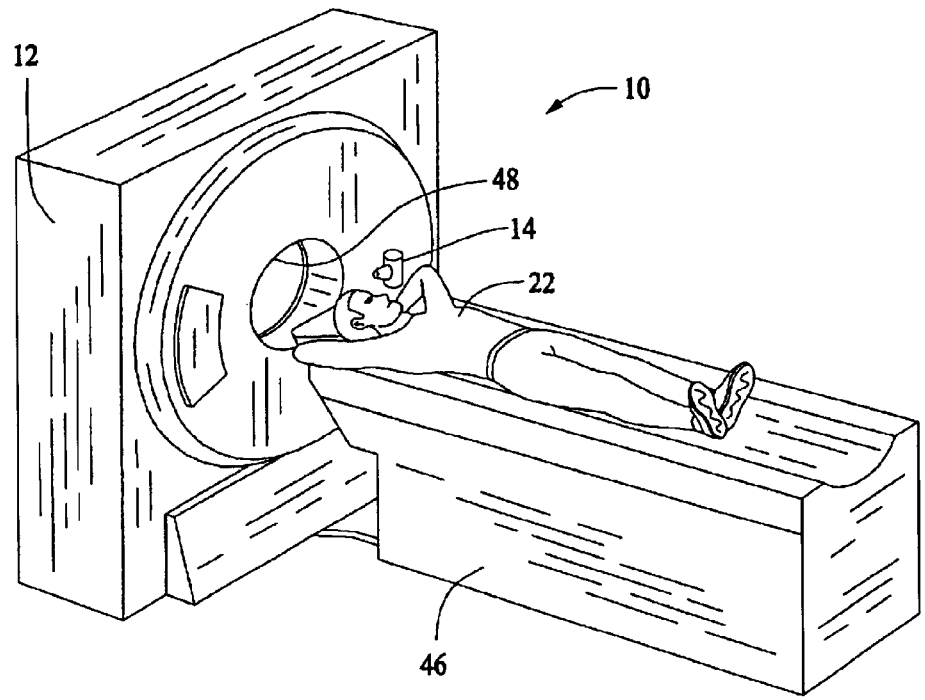
FIG. 1 is a pictorial view of a CT imaging system.
Figure 2:
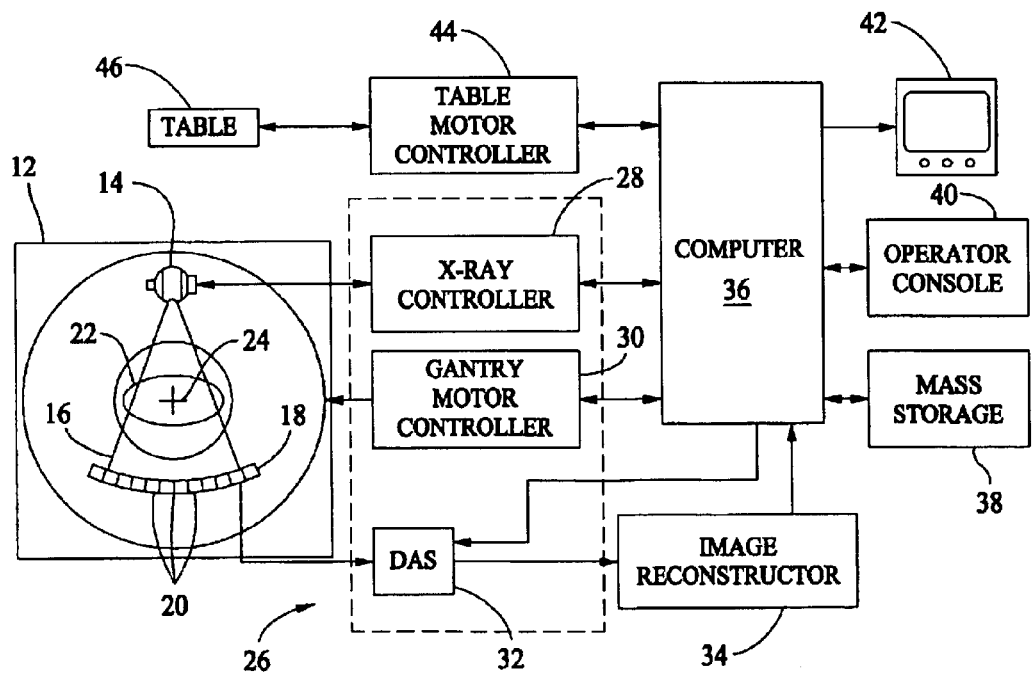
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
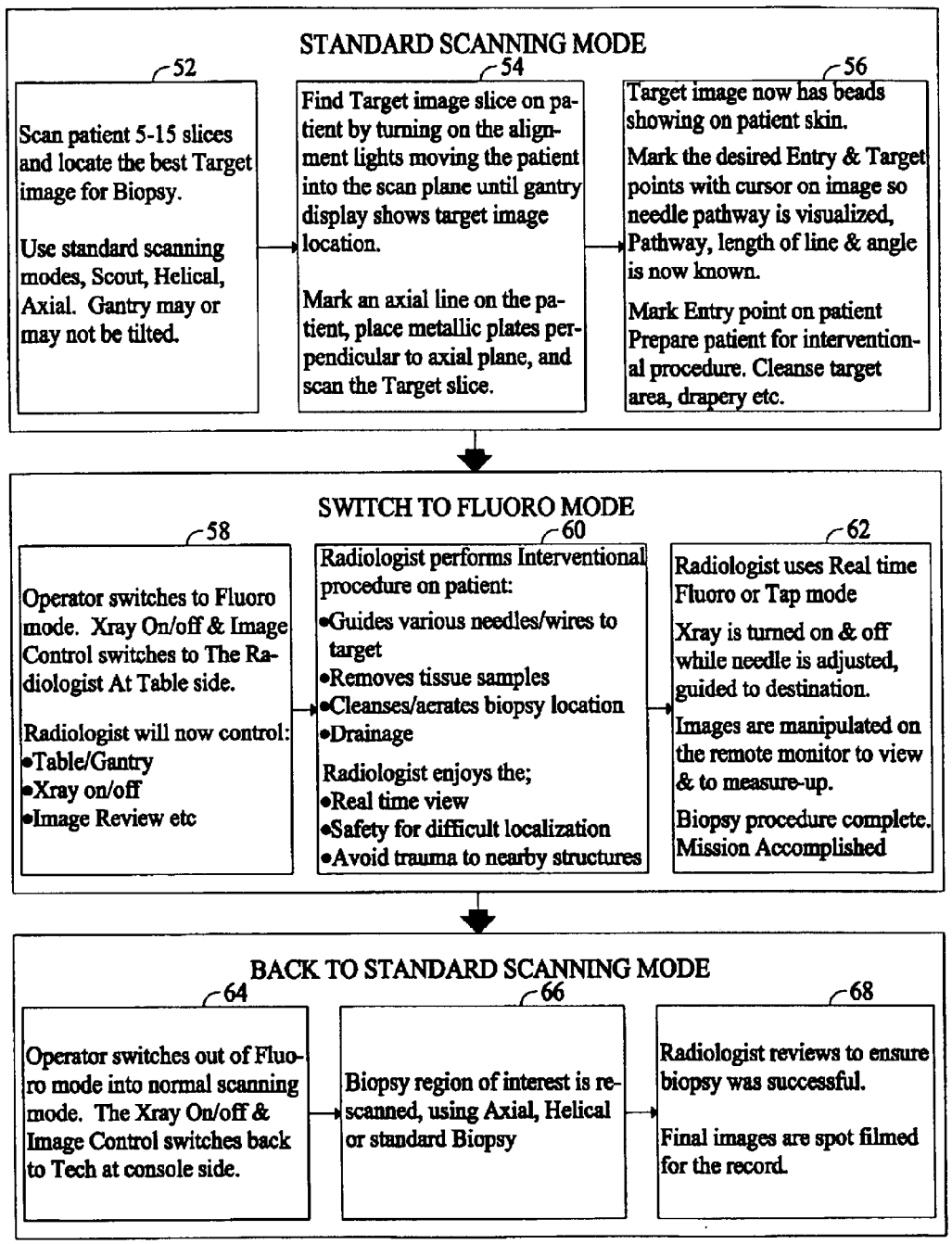
FIG. 3 is a flow chart illustrating the operator performed steps in connection with converting from a standard scanning mode to a fluoro mode using the present system.

FIG. 3 is a flow chart 50 illustrating the operator performed steps in connection with performing a fluoro scan using the present system. The description of the operator performed steps is provided to facilitate an understanding of the present CT Fluoro system and the many advantages provided thereby. It should be understood that the present invention is not directed to these operator performed steps. Rather, the present invention is directed to the CT Fluoro system itself. The following description of a fluoro scan procedure is therefore provided to facilitate at least a general understanding of the objectives of a CT fluoro scan procedure, including the operations performed by the system users.

Particularly referring now to FIG. 3, and in order to localize a target image 52, the patient is scanned (e.g., about 5–15 slices) to locate a target for the image biopsy. In localizing the target, standard scanning modes can be utilized. A target image is then located on the patient 54 by using the alignment lights on the gantry and moving the patient into the scan plane. An axial line may be marked on the patient, and metallic plates may be located perpendicular to the axial plan. The target slice is then scanned. The biopsy path from the skin to the target location 56 is then determined. Particularly, the desired entry and target points are marked with a cursor on the image being displayed so that the needle pathway can be visualized. The entry point also is marked on the patient, and the patient is prepared for the procedure.

The system control is then transferred to the radiologist inside the scanning room 58. Particularly, up to this point, the system control has been maintained at the control console by an operator. The radiologist now controls the fluoro scans using a foot pedal (x-ray on/off) and a controller located at the patient table. Using these controls, the radiologist controls the patient table, gantry, the x-ray source, and image review. The fluoro procedure is then performed 60. Specifically, the radiologist guides various needles and wires to the target location, removes tissue samples, cleanses/aerates the biopsy location, and drains fluids from the patient. Using the present system as described below in more detail, the radiologist is able to review real time images, which enhances safety for difficult localizations as well as facilitates avoiding trauma to nearby structures. With the control provided to the radiologist, the radiologist can operate in a real time fluoro continuous or tap mode 62. Particularly, the x-ray source can be turned on and off as desired while the needle is adjusted and guided to its destination. Further, images can be manipulated by the radiologist so that the desired image data is displayed. The image artifact caused by the long biopsy needle can be used for guidance, since the artifact casts a shadow along the needle pathway.

Once the procedure is complete, control is returned to the technologist at the system console 64. The system is then switched out of fluoro mode and to a normal scanning mode. The biopsy region of interest may then be scanned using any one of a variety of scan techniques 66 to determine the success of the procedure. The radiologist may then review the images to ensure that the biopsy was successful 68.

From the foregoing description of a CT Fluoro scan, it should be understood that in generating an image for display, increasing the frame rate provides many advantages including that the radiologist is provided with increased information regarding the location of a biopsy needle. In addition, by providing control of the system to the radiologist, the radiologist is better able to control the procedure being performed on the patient and may be able to complete the procedure more efficiently.

Figure 4:
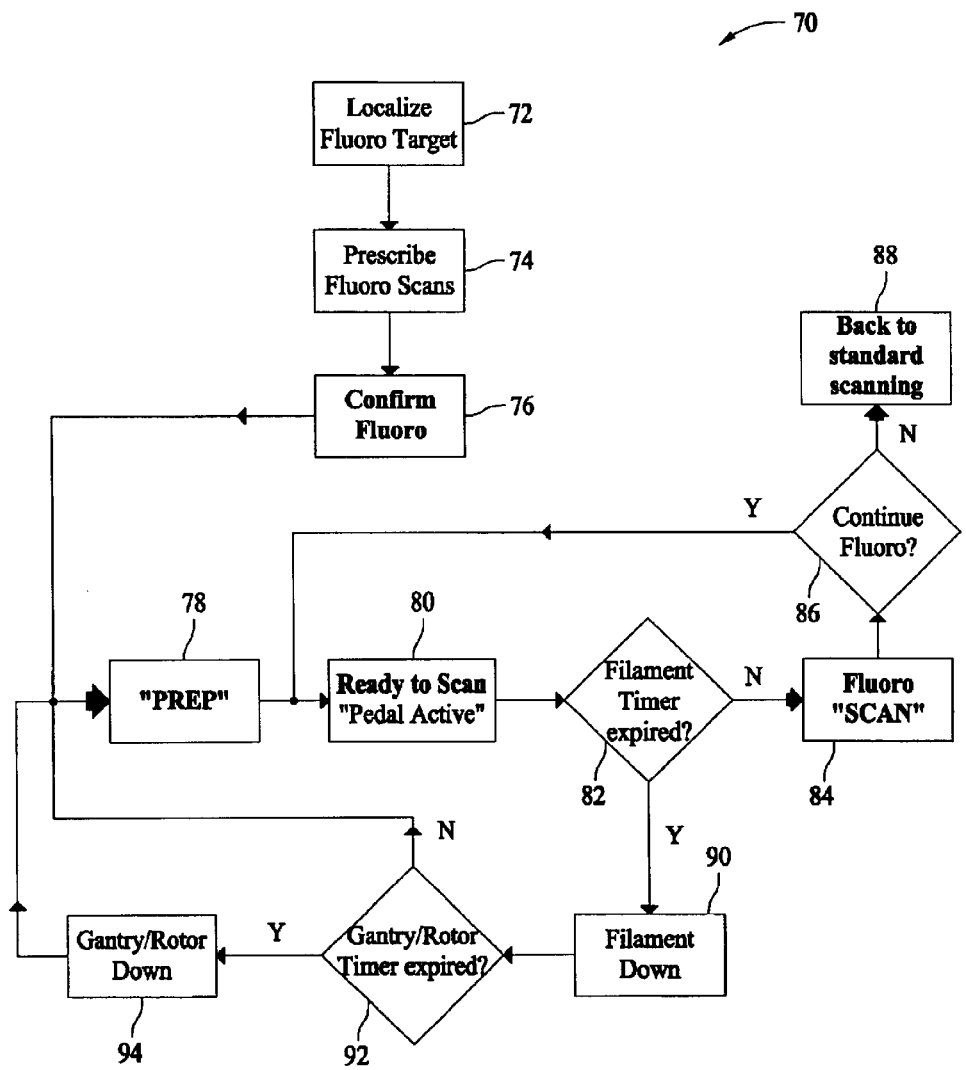
FIG. 4 is a flow chart illustrating the steps executed by the CT system in connection with execution of the fluoro scan.

FIG. 4 is a flow chart 70 illustrating the steps executed by the CT system in connection with execution of the fluoro scan. Particularly, and once the target is localized 72, the scans are prescribed 74, and the fluoro scan mode is confirmed 76 by the operator as described above, the system enters a prep mode 78 in which the gantry prep sequence is initiated. The gantry prep sequence is well known in the art. In the fluoro mode, the "prep" is controlled by the interventional radiologist from the patient table side using a control device. After completing the prep sequence, the system is ready to scan and the foot pedal at the patient table is activated 80.

The foot pedal is located on the floor on the patient side of the gantry. Provided that the x-ray source filament timer has not expired 82, the radiologist can perform the fluoro scan 84. Particularly, once the prep sequence is completed, a filament timer (e.g., about 90 seconds) is initiated. The radiologist can expend the 90 seconds of x-ray-on time over any length of elapsed time as needed by the fluoro procedure, until the total maximum allowed x-ray-on time has been used. If the operator releases the foot pedal, scanning can be reinitiated within about 2–3 seconds after the release. Specifically, if the foot pedal is released any time before the first full reconstructed image is displayed, the x-ray source will not be de-energized but will remain energized long enough to collect one full image worth of data and display that image. This mode of operation is referred to as the tap mode. If the foot pedal is released any time after sufficient data has been collected to reconstruct a full image, the x-ray source will be de-energized within about 300 msec, from the foot pedal release. This mode of operation is generally referred to as the continuous mode. If the operator elects to discontinue scanning 86, then the system returns to the standard scanning mode 88.

If the x-ray source filament timer does expire 82, then the x-ray source is de-activated 90. Also, if the gantry/rotor timer expires 92, the gantry/rotor is de-activated 94 and operations return to the prep sequence mode 78. If the gantry/rotor timer in not expired 92, then operations return directly to the prep sequence mode 70.

The following description sets forth in more the detail various operator controls provided on an integrated controller, image reconstruction, and image display. The integrated controller enables the radiologist to maintain control of the system throughout the fluoro scan. The image reconstruction algorithms are generally directed to increasing the image frame rate or reducing image artifacts, or both, in the CT fluoro scan. The image display generally provides enhanced images and control to the radiologist during a scan procedure.

Operator Control

Figure 5:
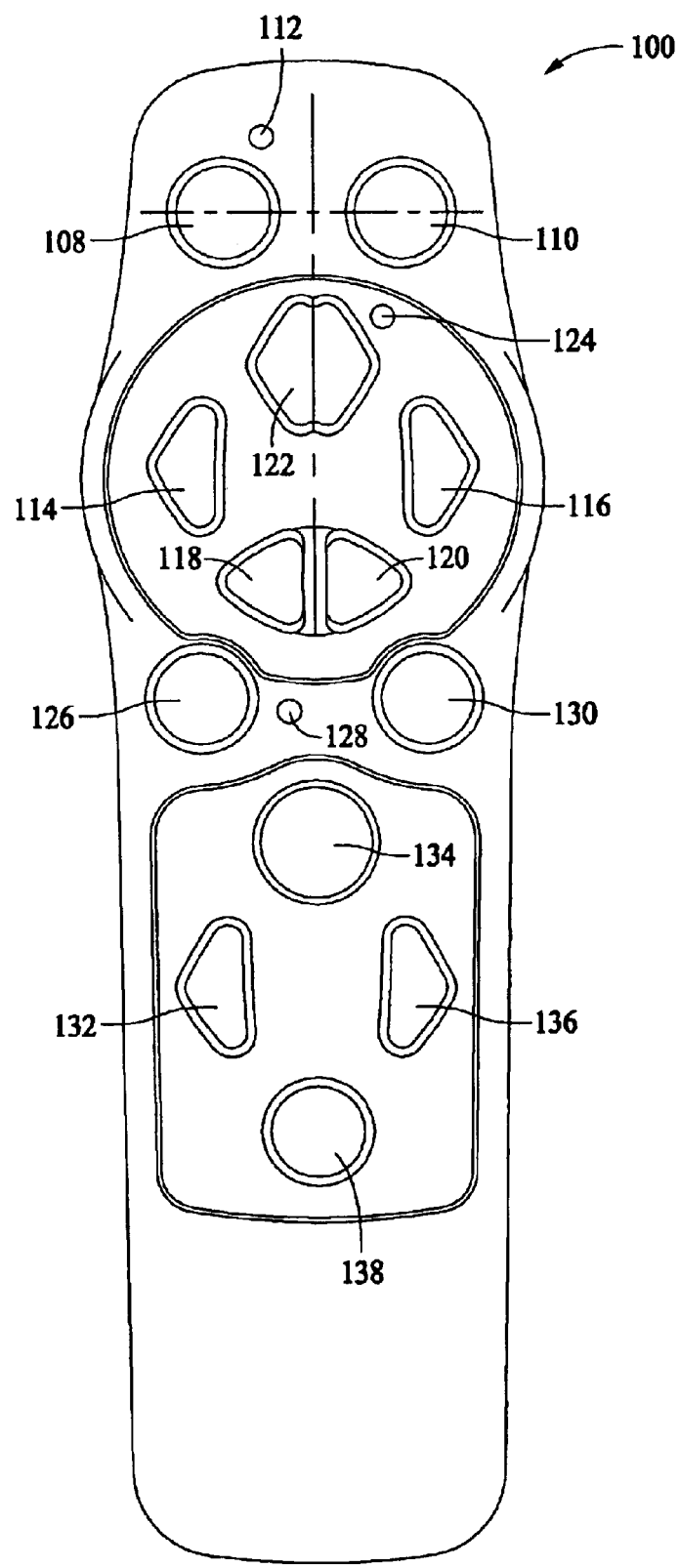
FIG. 5 is a schematic illustration of an integrated controller in accordance with one embodiment of the present invention.

The following is a detailed description of an integrated controller that may be used by an operator during a scan to easily and conveniently perform frequently executed operator tasks. More particularly, FIG. 5 is a schematic illustration of a handheld integrated controller 100 that may, be used in connection with imaging system 10. Particularly, controller 100 may be electrically coupled with computer 36 through interfaces between; table 46 and controller 44. Controller 100, alternatively, may be directly connected to computer 36. In any event, commands entered at controller 100 are communicated to computer 36 which then causes the commands to be executed.

Controller 100 is configured to be handheld, and the structure for making electrical contact, or connections, between push buttons and respective electrical contact pads, as well as the structure for communicating the selected command information to computer 36, are well known in the art. Particularly, by depressing a selected push button that corresponds to a particular command as described below, an electrical pulse or signal is supplied from controller 100 to computer 36. Computer 36 receives the signal and processes the signal to execute the particular command.

Generally, the commands executable via controller 100 can be described as scan and motion controls and image manipulation controls. The scan and motion controls are utilized for selecting scan parameters and well as controlling patient table motion. The image manipulation controls enable an operator to select various images and parameters for display.

Referring now particularly to FIG. 5, the location of the various command buttons on controller 100 may vary, and the present invention is not limited to any specific organization of the command buttons. By arranging the control buttons in the illustrated configuration, however, it is believed that an operator can easily and quickly locate the correct command button to execute the desire command.

With respect to scan and motion controls, command buttons for "prep" 108 and "alignment lights" 110 are provided. The prep command momentary or single push button and an LED 112 indicator is provided and function as follows. Particularly, when the protocol is loaded and the system control is switched to fluoro mode, prep button 108 will "back light" and flash at 0.5 second cycles as a prompt to the user to depress button 108 to initiate the prep sequence. When prep button 108 is depressed, the gantry prep sequence is initiated. With respect to LED 112, when LED 112 is off, the system is down or unarmed and the user must depress prep button 108. When prep button 108 is depressed, LED 112 will blinks at 0.5 Hz indicating warm up or arming sequence is initiated. LED 112 will continue to blink until the warm up or arming sequence is complete. LED 112 may illuminate as yellow during the warm up or arming sequence. When fully prepped, LED 112 will remain continuously on and may illuminate as green to indicate that the system is ready. If the system times out and the system prep shuts down, LED 112 is deenergized.

Alignment lights command button 110 is a momentary or single push button. While the gantry is rotating and the x-ray source is on, and when alignment lights command button 110 is depressed, the alignment lights are energized. When alignment light command button 110 is depressed again, the alignment lights are deenergized.

With respect to the alignment lights, and in one embodiment, three line generating (fan beam) laser modules are secured to the gantry and the laser light locates the scan plane on the patient while the gantry is rotating/scanning. The laser modules are spaced around the gantry rotating structure and are aligned with the scan plane. The gantry has a transparent window 360 degrees around the inner bore and as the gantry rotates with the alignment lasers on, the laser light is transmitted through the transparent window at all locations. This eliminates the strobing effect if only one or two lasers are used. The radiologist will see one continuous (spatial and temporal) line on the patient and needle holder. This line serves as a reference for the scan plane.

Scan and motion controls also include command buttons for "move table in" 114, "move table out" 116, "bump in" 118, and "bump out" 120 are provided. A move to scan 122 and an associated LED 124 for indicating move to scan also are provided. Scan and motion controls also includes an auto move command button 126 and LED 128, and a cradle float command button 130.

Move table in command button 114 is a deadman control (push and hold button), and depressing button 114 results in moving the table toward the back of the gantry at a constant speed, e.g., about 50 mm/sec. Move table out command button 116 also is a deadman control and moves the table toward the front of the gantry at a constant speed, e.g., about 50 mm/sec. For both move table in and move table out command buttons 114 and 116, when released (i.e., no longer depressed), table movement stops.

Bump in and bump out command buttons 118 and 120 are momentary or single push buttons. Depressing one of respective buttons 118 and 120 results in moving the patient in or out a preset or prescribed distance at a Constance speed, e.g., 5 mm or 10 mm at 5 mm/second.

Move to scan command button 122 (sometimes referred to as advance to scan button) is a push and hold or deadman type button. Depressing command button 122 results in moving the patient anatomy to a prescribed or indicated scan plan position at a constant speed, e.g., about 50 mm/second. Specifically, and during a fluoro procedure after the first acquisition, when command button 122 is depressed, the patient table is moved to the last acquired image/scan position. The table can be moved either forward or backward as a result of executing the command. Once the table is moved to the last acquired image/scan position, further scanning can be performed. LED 124 blinks at 0.5 Hz when the move to scan command can be executed, i.e., when the patient table is moved from the last acquired image/scan position. Once move to scan button is depressed, LED 124 remains on until the table reaches the last acquired image/scan position, and the LED 124 is off indicating that the table is now in position for scanning.

Auto move command button 126 and LED 128 are utilized when it is desired to provide constant movement of the patient table when the radiologist is inserting a needle at an angle oblique to the scan plane. By synchronizing insertion movement of the needle with movement of the table, the needle tip is maintained in the scan plane. More particularly, when the x-ray source is on, the operator depresses auto move button 126. While continuing to activate the x-ray/acquisition switch, the radiologist depresses either move table in command button 114 or move table out command button 116 to start the table moving at a constant speed (e.g., 3–5 mm/second) in the respective direction. Movement of the table may be limited to a preselected distance, e.g., 200 mm, to prevent movement of the table beyond a desired distance. To stop the auto move, the operator depresses auto move button 126, or when the x-ray switch is deactivated auto move is disabled. To return to auto move, the operator must once again depress button 126. LED 128 is on when in the auto move mode, and LED 128 is off when the system is not in the auto move mode.

Cradle float command button 130 is a momentary or single push button. When button 130 is depressed, the patient table is unlatched and free floating. The operator can then easily move the table to a desired position. A handle extending from the table can be provided to ease movement of the table without interfering with the patient. When button 130 is again depressed, the table latches in the selected position.

With respect to the image manipulation controls, "page reverse/forward" 132, "save" (or capture) 134, "grid" 136, and "preset window/levels" 138 command buttons are provided. By enabling an operator to perform these functions with controller 100, the system is believed to be easier to use and useful information can be displayed to the operator in an easily understandable format.

Particularly, reverse/forward button 132 is a double functionality control with a deadman control (push and hold button) and a momentary or single push button. Specifically, when button 132 is pushed and released as a momentary function, a command to advance or reverse one image for each button press is communicated to the display. When button 132 is pushed and held for more than two seconds, a command to display images in real time, e.g., 6 images per second, forward or backward (depending on the button pressed) will be communicated to the display. The images are stored in a memory buffer (e.g., the last 120 images are stored in the buffer) to enable such function. When button 132 is released, the play function stops.

Save button 134 is a momentary or single push button, and by depressing save button 134, a command is transmitted to the display so that the image then displayed on the screen will be captured or saved to the display memory buffer or database. The captured images can be recalled for display, analysis, filming, archiving, and networking.

Grid button 136 is a momentary or single push button. When grid display button 136 is depressed, a command is transmitted to the display so that a grid pattern scaled in square centimeters is superimposed over the image. Consecutive button pushes activate and deactivate the grid display.

Preset window/levels button 138 is a momentary or signal push button. Each time preset window/levels button 138 is depressed, a command is transmitted to the display to advance one predefined window/level setting. Alternatively, it is contemplated that one button push can cause the window/level setting to change in accordance with preprogrammed or defined settings selected by the operator. It is believed that the by limiting the defined setting to a maximum of 5 to avoid confusion. The setting name and/or values are displayed on the display screen with the image, and the command causes the display to sequence through window/level parameter settings in a continuous loop, advancing one setting with each push of the button. Sequencing typically occurs only in one ordered direction.

In addition to the functions described above, controller 100 could also include a track ball for measuring distances on the display, an x-ray scan initiation control, a view angle control for controlling, in real time, the view angle of the 3D image display, a "rock" control to rock the 3D image back and forth at a pre-determined speed, a gantry tilt control to control the gantry tilt angle, and a table elevation control of controlling the elevation of the patient table. For example, although no control button is shown on controller 100 for gantry tilt, it is contemplated that in addition to the foregoing, a gantry tilt control button could be included on controller 100. Enabling the operator to control gantry tilt at controller 100 will enhance the ability to control the fluoro procedure and allows the operator to bring the tip of the needle into view and follow it. Gantry tilt mechanisms are known and typically include stepper motors electrically connected to the gantry. Such tilt control can be enabled while fluoro scanning is in progress.

Of course, not all of these controls described above need be incorporated into the controller, and any one or combination of these controls or commands (along with other commands) could be executable by such controller. By enabling an operator to initiate command execution with an integrated controller as described above, it is believed that CT Fluoro procedures can be performed more efficiently and quickly than with known systems. The controller also is believed to be very convenient to use, therefore increasing the likelihood that operators will take advantage of its benefits.

Image Reconstruction

As explained above, increasing the frame rate without significantly deteriorating image quality provides an operator with increased information during the CT Fluoro scan. Set forth below are descriptions of various algorithms that can be utilized to achieve this objective. The algorithms can be utilized in a system by themselves or in any combination depending upon the desired results.

A. Dynamic Collimation

In known system, slice thickness does not change during a CT Fluoro procedure. For example, a 10 mm slice thickness is used throughout the procedure. The collimator slice thickness typically is a compromise between resolution and volume coverage. If the collimation is too thin, however, a very small volume will be covered and there is an increased probability that the needle will move outside the scanning slice. If the slice thickness: is too large, very little z-axis resolution will be provided and mis-positioning may result. For example, if the object is 5 mm in diameter, a 10 mm slice thickness is not sufficient to ensure that the biopsy needle is positioned inside the object.

In accordance with one aspect of the present invention, the pre-patient collimator initially is selected to have a thick collimation (e.g., 10 mm). After the needle is positioned close to the target object, the collimator is dynamically changed to a thinner slice (e.g., 5 mm).

More particularly, and in one embodiment, the controller (e.g., controller 100 shown in FIG. 5) could include a control button for changing the collimator aperture. Apparatus required to change the collimator aperture is known in the art. The change of the collimator aperture occurs during the x-ray off time. For example, a collimator "up" and "down" button could be provided on the controller to increase and decrease the aperture size.

With the above described dynamic collimation, more detailed examination of the region can be provided. Since the needle is positioned near the target, the probability of having the needle outside the scanning volume is reduced.

The foregoing described dynamic collimation can be performed with both single slice and multislice detectors. With a multislice scanner, for example, the multislice detector initially is configured to generate four 5 mm slices. After positioning the needle, the detector can be dynamically configured to generate four 2.5 mm slices.

B. Fast Image Update

A known system architecture limits the reconstruction speed to less than or equal to 6 frames per second. In order to increase the frame rate, significant hardware and/or software changes are believed to be necessary. Particularly, only six 256 by 256 memories are available to the backprojector. To further improve the reconstruction speed, software changes would be required to provided two additional image memories are needed or more memory can be added by hardware modifications.

Rather than hardware or software modifications, however, image interpolations/extrapolation can be performed to fill in the gaps between the reconstructed images. Image extrapolation can be utilized to estimate an image $P_N$ based on several previous acquired images. For example, the Nth image can be determined in accordance with the following:

$$P_n = \sum_{N-m}^{N-1} a_i P_i \quad (1)$$

where $\alpha_i$ is the coefficient of extrapolation. Using the above described extrapolation, the frame rate can be easily doubled, tripled, or quadrupled depending on the display processor capability. Rather than being linear extrapolation as described above, the extrapolation could be non-linear (high order), recursive, or non-recursive.

C. View Compression and Expansion

To reduce the amount of data to be processed, a selective view compression algorithm can be utilized. Of course, reducing the amount of data to be processed provides the advantage of decreasing the amount of time required to generate an image during a fluoro scan. For example, one known CT system uses 984 views for image generation to avoid aliasing artifacts. The time taken for the tomographic reconstruction is directly proportional to the number of views used and therefore, by reducing the number of views used in image generation, the reconstruction can be sped up. The image quality should, of course, be maintained at an acceptable level.

More particularly, in an exemplary embodiment, the objective is to generate multiple images in as short a time as possible. To accomplish this objective, the images are reconstructed only with standard algorithms in a 256 by 256 matrix (i.e., no specialized processing is performed) and slight image quality degradation is acceptable, particularly since the main purpose for displaying the images is to guide the insertion of the biopsy needles.

Generally, with view compression, the view angle increment in the new data set preferably remains a constant. That is, the angles between the compressed views are the same throughout the entire data set. By maintaining the view angle increment constant, the reconstruction process is simpler and also is believed to be optimal for reducing aliasing artifacts since the view aliasing is determined by the largest angular spacing between views, not the average. Therefore, the compression algorithm preferably maintains the view angle increment constant.

The following algorithm satisfies the above described property, i.e., maintaining the view angle increment constant. More specifically, and in an exemplary embodiment, every even view in the compressed data contains unmodified projection in the original data set, and every odd view in the compressed data set consists of the average of the two views in the original data set. The new projection data set is generated in accordance with the following:

$$p_{compressed}^{(k)} = \quad (2)$$
$$\begin{cases} P_{original}\left(\frac{3k}{2}\right) & k = 0, 2, 4, \ldots \\ 0.5\left[p_{original}\left(\frac{3k-1}{2}\right) + p_{original}\left(\frac{3k+1}{2}\right)\right] & k = 1, 3, 5, \ldots \end{cases}$$

Different kernels can, of course, be used in the compression process. The simple average described above is only for the ease of illustration. In addition, the even or odd views in the equation are interchangeable, i.e., the odd views could be unmodified and the even views could be averaged.

With $\Delta\theta$ denoted as the angular increment in the original data set, the angular increment in the new data set is $3\Delta\theta/2$. Therefore, using the above described algorithm, the number of views used in reconstruction is only ⅔ the number of original views. For example, if the original data contains 984 views for $2\pi$ rotation, the new data set has 656 views per $2\pi$ rotation, which is a 33.3% reduction.

The following discussion relates to combating aliasing artifacts by expanding the views. Particularly, reducing the number of views used in the reconstruction process results in view aliasing artifacts in the reconstructed image. To reduce the aliasing artifacts, the present algorithm may be utilize to generate additional view data that can be utilized in the backprojection process to reduce aliasing artifacts.

Figure 6:
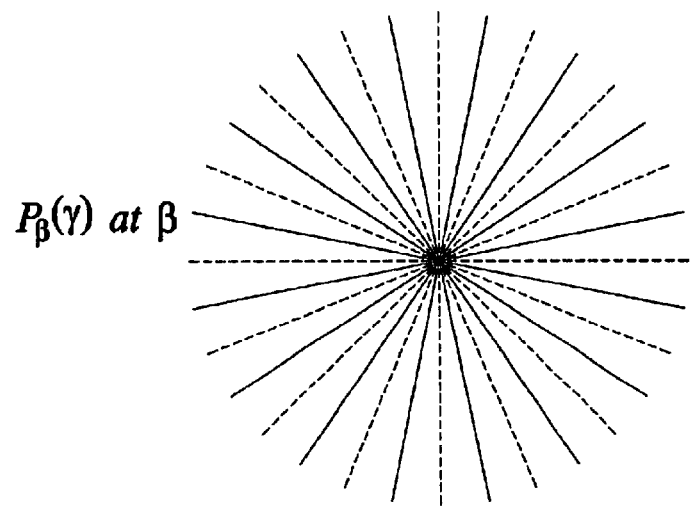
FIG. 6 is a graphical illustration of actual projection data and generated projection data used in connection with reducing aliasing artifacts.

More particularly, the present reconstruction algorithm differs from standard filtered backprojection algorithms only in the backprojection step, and the difference is graphically illustrated in FIG. 6 where the solid lines indicate the set of gantry angles β at which a set of projection data is physically collected. For the purposes of the following discussion, $\rho_{62}(\gamma)$ represents the filtered version of the projection data set. The standard filtered backprojection algorithm backprojects $\rho_{62}(\gamma)$ from the gantry angles β.

In accordance with the present reconstruction algorithm, a second set of filtered projection data is generated for a second set of gantry angles, illustrated as dashed lines in FIG. 6 which bisect the first set of gantry angles β Simple linear interpolation can be used, for example, to compute the second set of filtered projection data from the first set of data $\rho_\beta(\gamma)$.

Both sets of data, i.e., the actual data and the generated data, at the corresponding gantry angles are then backprojected, and the image is reconstructed using such data. The backprojection can be implemented, for example, on an image generation (IG) board in a pipe-line fashion to increase reconstruction speed. Of course, more views can be used for higher order interpolation. Also, more than two views can be generated between views.

The above described algorithm degrades the azimuthal resolution of the image. When other azimuthal-resolution limiting factors, such as the detector primary speed, are considered, the additional degradation may be unnoticeable or acceptable.

D. Channel Compression with Filter Kernel Boost

For computational speed-up, each projection channel may be formed by two detector channels or cells. Particularly, the cells are ganged, e.g., double ganged, so that the ganged cells generate one output, or projection channel. In the exemplary embodiment described below, it is assumed that the cells are double ganged. However, a higher compression ratio can be used. The ganging is described as follows:

$$\xi'_k = \xi_{2k} + \xi_{2k+1} \quad (3)$$

The channel ganging can be performed, for example, immediately after air-calibration (Air-cal) correction. As is known in the art, the Air-cal correction includes normalization, channel expansion, Qcal (i.e., image calibration), theta fix, and cross-talk corrections. Alternatively, the channel ganging could be performed immediately after the detector primary speed/afterglow correction to achieve the maximum speed advantage. The above described processing preferably is carried out prior to the Air-cal correction (i.e., prior to normalization, channel expansion, Qcal, theta fix, and cross-talk correction).

Due to channel ganging, many of the calibration vectors applied after the Air-cal correction need to be modified to reflect the fact that each new channel now represents two of the previous channels. The affected vectors are, for example, beam hardening vectors. For the three beam hardening vectors, $B^1$, $B^2$, and $B^3$, the following relationships are used to generate new vectors:

$$B'^1_k = 0.5(B_{2k}^1 + B_{2k}^{1+1})$$

$$B'^2_k = 0.5(B_{2k}^2 + B_{2k}^{2+1})$$

$$B'^3_k = 0.5(B_{2k}^3 + B_{2k}^{3+1}) \qquad (4)$$

Since the vectors are generated prior to the "recon-loop", modification to the vector generation process should not affect the reconstruction performance in terms of speed.

One direct impact of the double channel ganging on the image quality is reduced spatial resolution. For example, the smallest object that a CT fluoro system needs to resolve is 5 mm. To at least partially compensate for the loss of resolution, a reconstruction filter kernel boost can be utilized. Particularly, the reconstruction filter (in frequency domain) is multiplied by a window function which has a higher magnitude in the mid to high frequency range, such as the following window function:

$$w = 1 + \alpha_1 f + \alpha_2 f^2 + \alpha_3 f^3 + \alpha_4 f^4 \qquad (5)$$

where $\alpha_1$, to $\alpha_4$ are parameters. In one specific embodiment, the parameter set of $\alpha_1=0.0$, $\alpha_2=0.6$, $\alpha_3=0.2$, and $\alpha_4=0.0$ is utilized.

The above described filter kernel boost can also be applied to other situations where system resolution needs to be improved due to other factors. For example, reconstruction kernel boost can be utilized to compensate for the degradation of resolution due to the removal of a frequency domain interpolation process. Particularly, the projection data after the Fourier transform is replicated before being multiplied by the filter kernel. This process equals performing the interpolation in frequency space, since the filtered projection after this process will be doubled in terms of the number of sampling points. Since the interpolation is performed in frequency space, it preserves the frequency contents in the projection. This process, however, is computationally expensive, since it increase the size of the Fourier transform by a factor of 2. For reconstruction speed, it may be desirable to perform the interpolation in the spatial domain. For example, a 4-point Lagrange interpolator can be used. However, a slight degradation in system resolution will result. This can be compensated for by pre-multiplying the filter kernel by a window function (Equation 3). For the standard and soft reconstruction kernels, the parameter set $\alpha_1=0.0$, $\alpha_2=0.1$, $\alpha_3=0.3$, and $\alpha_4=0.0$ can be utilized.

E. Filtering

To reduce patient motion artifacts, the weighting scheme described below can be utilized to minimize the amount of filtering performed on each view. Particularly, for CT fluoroscopy applications, and in an exemplary implementation, images are generated at 6 frames per second with the gantry rotating about the patient one resolution per second. Therefore, highly overlapped reconstruction is performed. In other words, each projection is used in the generation of multiple images. Since the filtering process is the most time consuming portion of the reconstruction, it is desirable to avoid repeatedly filtering each projection for each reconstructed image.

Accordingly, an overscan weighting algorithm can be utilized. Since the overscan weight is constant along the channel direction, the filtering operation and weighting operation can be reversed and only one filtering per projection is needed. Each filtered projection can then be multiplied by different weights prior to the backprojection. The overscan weighting algorithm is performed in accordance with the following.

$$w(\gamma,\beta) = 3\theta^2(\gamma,\beta) - 2\theta^3(\gamma,\beta) \qquad (6)$$

where $$\theta(\gamma,\beta) = \begin{cases} \dfrac{\beta}{\beta_0} & 0 \leq \beta < \beta_0 \\ 1 & \beta_0 \leq \beta < 2\pi \\ \dfrac{2\pi + \beta_0 - \beta}{\beta_0} & 2\pi \leq \beta < 2\pi + \beta_0 \end{cases}$$

where $\beta_0$ is a parameter which specifies the overscan angle. The parameter $\beta_0$ is determined based on the best compromise between image quality and reconstruction speed.

The above described weighting de-emphasizes the contributions from the start and end of the scan. For each view, the tomographic reconstruction filter is applied first, followed by multiplying the views by at least two different weights, then followed by backprojecting the weighted views to at least two different image locations. The content of each image memory is then transferred and initialized after a pre-determined number of views are accumulated.

Figure 7:
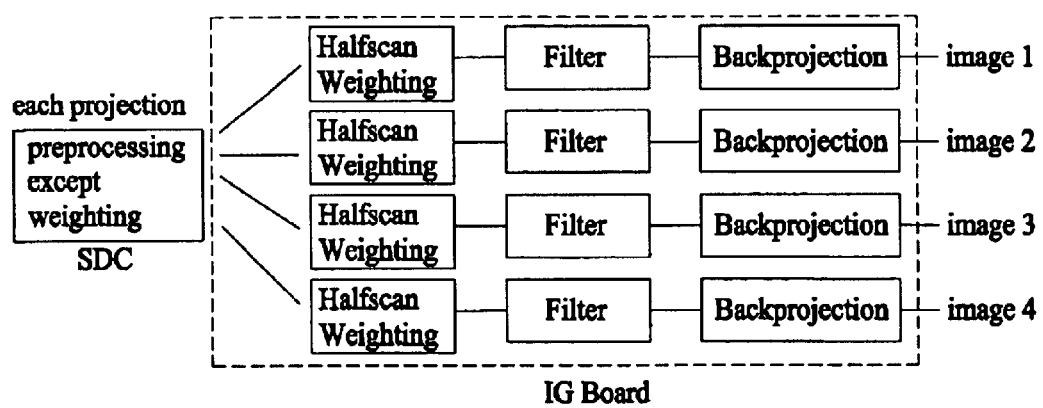
FIG. 7 is a schematic illustration of an exemplary image generation board.

In addition, halfscan weights with multiple processors to perform multiple filtering can also be utilized. Particularly, assume that at a given image frame rate, each projection contributes to N images at most. For example, N=2 for 3 frame/rotation and N=4 for 5 frame/rotation. The data processing architecture illustrated in FIG. 7 can be used for simultaneous multiple images reconstruction. Segmented reconstruction is utilized for the best temporal resolution. Also, only two branches are needed for 3 frame/rotation. The bottleneck of the architecture is the filtering step, which can be sped up by eliminating Fourier domain interpolation, and, 2:1 channel compression.

A faster frame rate can be achieved by adding a second image generation board. Also, some preprocessing and post-processing steps can be bypassed to further speed up the data processing.

F. Backprojection

In the CT Fluoro mode, since six different images are under reconstruction at any time, the multiple weighted projections needed for these images are loaded into the backprojector memory at one time. Based on the selected overscan angle, the number of weighted projections can be reduced to speed-up the data transfer to the backprojector memory. More particularly, and in an exemplary system, for every ⅙th of the overscan rotation, a complete image is generated at one location. The backprojector memory therefore is divided into 6 sub-regions. At each time instance, a filtered projection is weighted with different overscan weights and backprojected into all six sub-regions. In one specific implementation, for example, 696 views are required to generate a complete image. Therefore, after the 696th projection is backprojected, the first complete image is pulled from sub-region number 1. 116 views later, a second complete image is pulled from the sub-region number 2. The process repeats after the completion of the 6th image.

In the exemplary system, the reconstruction board is divided into 8 parallel pipes and since 6 images/overscan rotations are generated, the number of views used for each image generation needs to be divisible by 48 (i.e., 6 times 8). The above described selection is not divisible by 48 (i.e., 696 is not divisible by 48). It is undesirable, of course, to significantly increase the overscan angle (e.g., the smallest number larger than 696 and divisible by 48 is 720, which corresponds to an overscan angle of 35.1 degree), because lag will be significantly increased. It also is undesirable to significantly reduce the overscan angle (e.g., the largest number smaller than 696 and divisible by 48 is 672, which corresponds to an overscan angle of 8.8 degrees), because patient motion artifacts will significantly increase.

Accordingly, and to increase the speed of backprojection, and rather than starting each image at the multiple of 116 views, the second image is started at view 120. The third image starts 112 views after the second image. The fourth image starts again 120 views later. The fifth image is further delayed by 112 views. This process continuous.

More generally, let N denote the number of views required to generate a complete image. Also, let X denote the number of parallel processing pipes, and Y denote the number of images generated per N-view-rotation. If N is divisible by Y and not divisible by (XY), the starting view number for the consecutive images can be alternated at (N/Y)+X/2 and (N/Y)−X/2 views after the starting view of the previous image. The order is interchangeable.

The above described backprojection algorithm avoids significant penalties on system delay and image artifacts. There is, of course, a very slight non-uniform time interval between images, which varies by a few milli-seconds. Further, if the backprojector has sufficient speed, each projection can be backprojected a number of times, e.g., 6 times. The backprojected view can then be scaled and added to different image memories.

Figure 8:
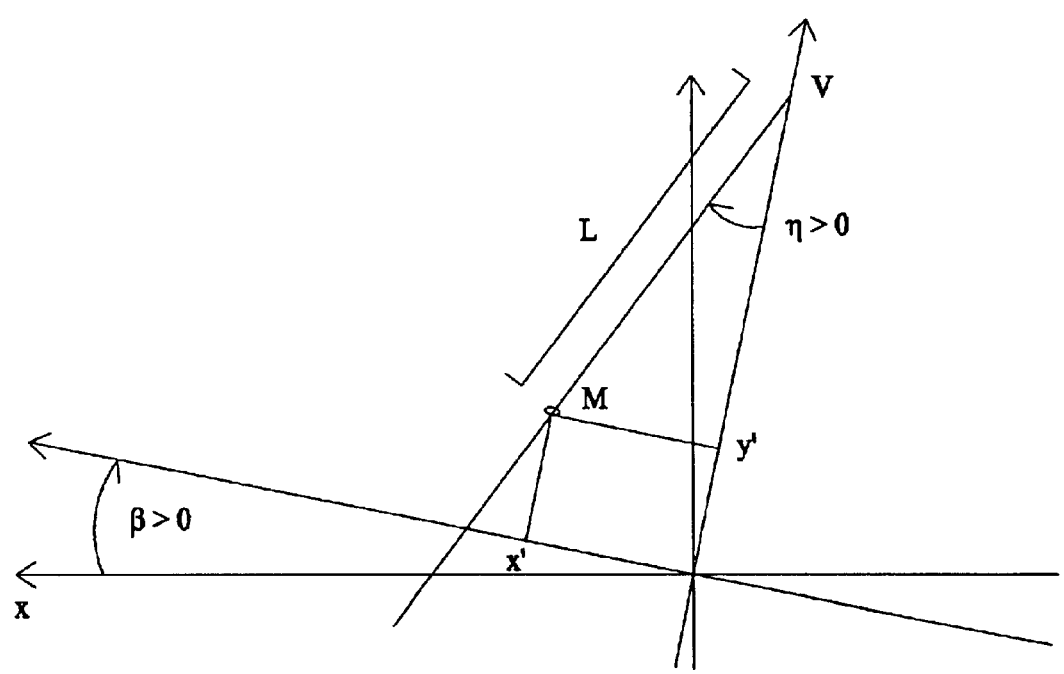
FIG. 8 illustrates a fan-beam projection for a view angle $\beta$.

In addition, a simplified backprojection technique can be used under the conditions where backprojection is the bottle neck of the reconstruction process. More particularly, the basic image backprojection operations are as follows. Each filtered projection is backprojected onto the image through a loop over the reconstruction grid pixels. Considering the patient coordinate system (x,y) and the rotated coordinate system (x',y') associated with the current view (FIG. 8) the backprojection relies on a calculation of the fan angle η q (view and pixel dependent), to perform an interpolation of the appropriate projection data. Back projection also requires calculation of $(1/L)^2$, where L=L(β,x,y) is the pixel to fan—vertex distance (view and pixel dependent). By linearizing η and $(1/L)^2$ around $\beta_0$ and $(x_0, y_0)$, then:

$$\eta(\beta_0+d\beta) \approx \eta(\beta_0)+A \times d\beta \qquad (7)$$

$$\frac{1}{L^2(\beta_0+d\beta)} \approx \frac{1}{L^2(\beta_0)} + B \times d\beta \qquad (8)$$

In the view-to-view only linearization application, a full calculation of the quantities η and $(1/L)^2$ takes place every M views, where M is a parameter. For each other view, the quantities are estimated using linear interpolation. In practice, it is simpler to calculate the linear approximation by relying on a pre-calculation of the next view to be fully processed. In the view-to-view and within view linearization, the method the same method described above except that for those views which were previously fully processed, calculation for η and $(1/L)^2$ occurs only once every P pixels, and the values in between are linearly interpolated.

The backprojection equations are:

$$\hat{x} = \frac{x'}{S}; \hat{y} = \frac{y'}{S} \qquad (9)$$

$$\tan\eta = \frac{x'}{S-y'} = \frac{\hat{x}}{1-\hat{y}}; \text{Let } U = \frac{1}{1-\hat{y}}:$$

$$\eta = \text{atan}(\hat{x} \times U); \left(\frac{1}{L}\right)^2 = \left(\frac{S}{L \times \cos\eta}\right)^2 = U^2$$

These relationships serve as the basic relationship from which the fan angle and the inverse-squared of the distance from the fan-vertex to the pixel are determined. Simplifying these relationships provides significant computational savings. In particular, in the view-to-view linearization approach, the following relationships apply:

$$\eta(\beta_0+d\beta) \approx \eta(\beta_0)+A \times d\beta \qquad (10)$$

$$A = \frac{S^2}{L^2}[\hat{y}(1-\hat{y}) + \hat{x}] \qquad (11)$$

and:

$$\frac{1}{L^2(\beta_0+d\beta)} \approx \frac{1}{L^2(\beta_0)} + D \times d\beta \qquad (12)$$

$$D = \frac{-2\hat{x}}{L^3(\beta_0)} \qquad (13)$$

Parameters A and D do not have to be determined using equations (11) and (13). Instead, A and D may be estimated from a "look-ahead" full calculation for views N and N+M. For the views in the interval ]N,N+M[, calculations in equation (9) are skipped and replaced by a linear approximation based on estimating A and D from views N and N+M.

G. Parallel Processing

To further speed-up the reconstruction process, it is contemplated that many processes can be performed on different processors in parallel. For example, the pre-processing, filtering, backprojection, and post-processing can each be performed on different processors. With such a configuration, and while one processor is processing view i, a different processor can process view i+1. Further, while the backprojector is processing image number i, the post-processing unit can process image number i−1.

Image Display

Set forth below is a description of image display apparatus and algorithms that may be implemented in a CT Fluoro system to provide enhanced imaging. The apparatus and algorithms can be utilized in a system by themselves or in any combination depending upon the desired results.

A. Partial Image Display

As explained above, an important performance parameter for a CT Fluoro System is the time to first image. By generating a first image more quickly, the operator is provided with more information and should have a better sense of control since timely feedback is provided. Accordingly, and to reduce the time to first image, a partially reconstructed image can be displayed. For example, a set of images can be produced using ⅙ to ⅚ of the full views and overscan weights. The views can be displayed at roughly a rate of 6 frames per second. In one specific system, the partially reconstructed images can be displayed when 120, 232, 352, 464, and 584 views are accumulated in the first image generation memory buffer. The overscan algorithm may, for example, be the overscan algorithm described in copending U.S. patent application Ser. No. (15-CT-4313), entitled Image Reconstruction In A Computed Tomography Fluoroscopy System, which is assigned to the present assignee and incorporated herein, in its entirety, by reference. The overscan angle may, for example, be 22.0 degrees.

Generally, the partially reconstructed image is obtained with the weighting scheme. Since most of the motion artifact suppression weights (e.g., overscan weights) suppress the contribution from the start of the scan and gradually increase the contribution of the views to the final image, overscan weighting presents a smoother transition from image to image as the partially reconstructed images are displayed, as compared to no weights. Of course, other weighting schemes can be used.

B. Dynamic Image Reformation

Examining the needle position from different orientations, i.e., views, sometimes is desired. To address this need, dynamic image reformation can be performed. Particularly, axial images are displayed at a very high rate and the operator may reformat the axial images and display the reformatted images in real time. The operator may therefore view the needle from different angles and obtain depth information.

The image reformation may be performed by image interpolation. Particularly, image reformation refers to viewing a cut-through plane of an object. That is, in a conventional CT display, a series of images perpendicular to the z-axis are generated and displayed. If the same object is desired to be viewed along a plane that is in alignment with the z-axis which forms a 45 degree angle with the x-y axis, then the intersection of this new plane with the set of planes that represent the CT image is determined. Once the intersections are determined, a reformatted image can be formed by linear interpolation of the original CT images along the intersections. Image reformation algorithms are known.

C. Flat Panel Display

To provide improved display, a flat panel display may be utilized. Such displays are commercially available, and one display suitable for use in CT Fluoro systems in Model No. ATC1245B of Allus Technology Corp., 12611 Jones Road, Houston, Tex. 77070. The display, in one embodiment has a 1280×1024 pixel configuration, good image resolution, and has about a 15"–17"diagonal size. The display may, of course, be smaller or larger.

The display is ceiling suspended. Such ceiling suspension system are commercially available, and one suspension system suitable for use in CT Fluoro systems is Model No. 6262 of Mavig, 202 Whistle Stop, Pittsford, N.Y., 14534. The suspension system is located at the gantry perimeter for access to the display from front/back and right/left sides. The suspension system allows four axis of positionability and can be positioned close in the gantry bore area. The suspension system also is counter poised for easy placement/adjustment by an operator, and can be moved quickly for access to a patient. The display also should have a wide viewing angle to accommodate two viewers and should be a color display to provide an enhanced user interface.

D. In-Room Display

Figure 9:
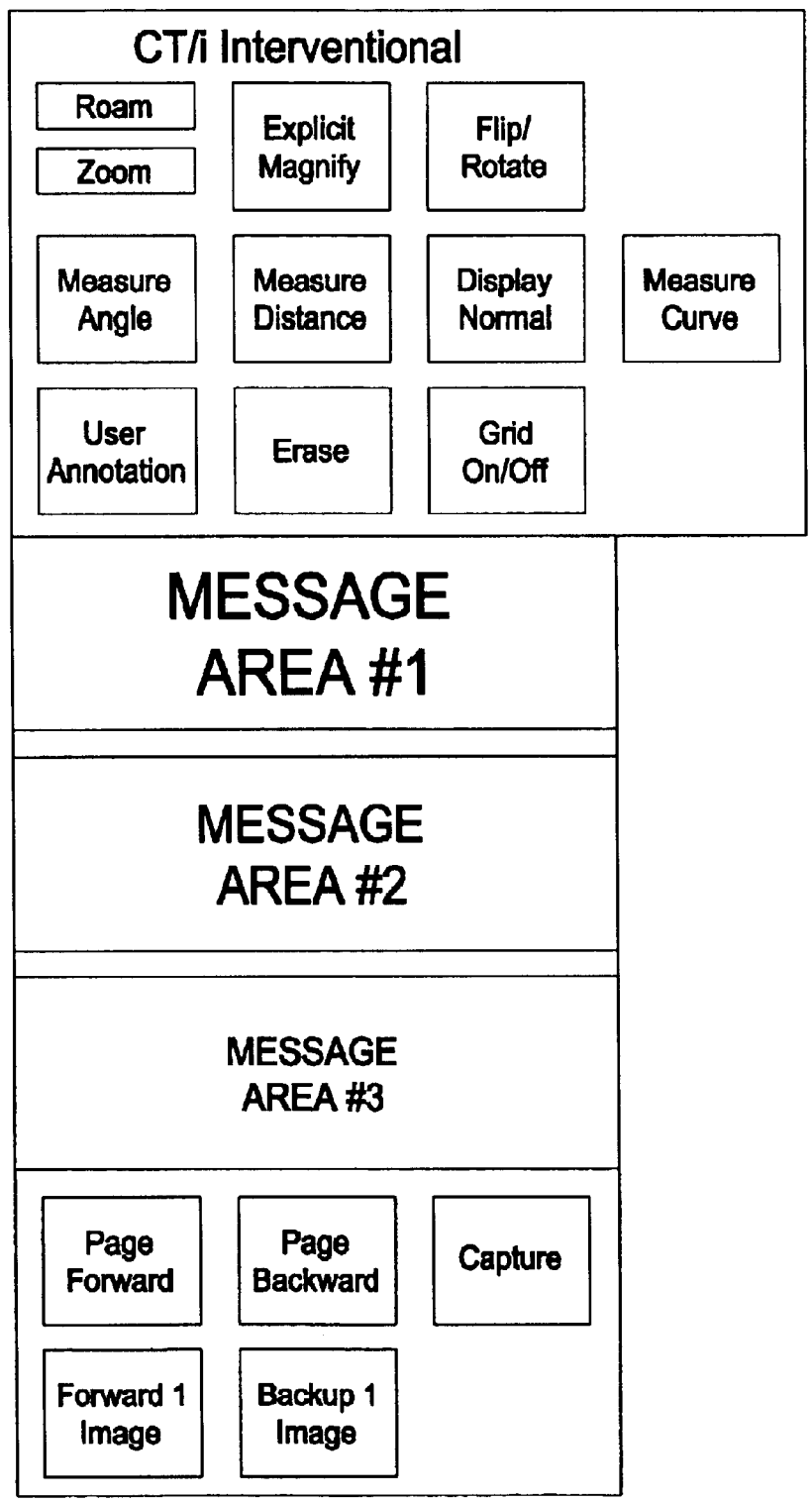
FIG. 9 illustrates a user interface for use with a CT Fluoro system display.

A user interface for use with a CT Fluoro system display is illustrated in FIG. 9. Display includes a CT/i Interventional control, three message areas (hierarchical and designated as message area #1, message area #2, and message area #3), and an image control. Interventional control enables the operator to analyze and manipulate images for view on the display. For example, control includes commands for roaming and zooming, for magnifying, and for flipping/rotating an image. Control also includes commands for measuring an angle, distance, and curve. A control command also is provided to return the display to the normal display mode of operation.

Control further includes a command to allow user annotations to be added to an image, and a command to erase annotation. A grid on/off command also is provided which enables a user to have a grid pattern scaled in square centimeters superimposed over the image being displayed.

Messages are displayed in the respective message areas. The most urgent messages are displayed in area #1, less urgent messages are displayed in area #2, and the least urgent messages are displayed in area #3.

Image control includes page forward and page backward commands. The page forward and page backward commands allow the operator to page through the messages displayed in areas #1, #2, and #3 to find the desired message. The forward 1 image and backup 1 image commands enable the operator to select an image for display. The capture command enables an operator to save the image then displayed on the screen to the display memory buffer or database. The captured images can be recalled for display, analysis, filming, archiving, and networking.

The display may also includes two clocks indicating the x-ray exposure time. Particularly, the first clock indicates the exposure during a single run. Whenever the foot switch is initiated, the clock starts to count the number of seconds that the patient is exposed to the x-ray. Specifically, each procedure presently is limited to 90 seconds of exposure, and this first clock helps the operator to better control the patient exposure as well as the timing. The second clock indicates the accumulative exposure time to the patient. For example, during each biopsy operation, multiple x-ray "burst" can be initiated. Between the bursts, the operator will have time to consider the best approach for the next burst. The second clock keeps track of the total amount of exposure performed up to the current time. The clocks serve as indicates that could be either time (length of exposure), total mAs (tube current multiplied by time), or some type of total dose measure to the patient (e.g., organ dose or skin dose) based.

E. Magnification

Real time magnifications of digital images are needed in many applications. Some magnification methods, such nearest neighbor and bilinear interpolation, are included in general purpose graphic packages and optimized for execution speed an specialized hardware. But higher quality magnification algorithms such as bicubic interpolation are not included. Hence the need arises for methods that approximate bicubic interpolation, but use routines that are accelerated.

As described below in more detail, algorithms for altering the spatial characteristics of digital images can be utilized for such magnification. Generally, one algorithm uses a two pass scheme in which each of the passes represents interpolation in the x and y directions respectively. Bicubic interpolation in each direction is approximated using linear interpolation followed by a one dimensional convolution filter. The other algorithm applies bilinear interpolation first, followed by a two dimensional convolution filter. The methods can be practiced using the OpenGL graphic package, which is well known in the art. Also, the linear, bilinear, cubic and bicubic interpolations are well known procedures, along with the linear least squares estimation method. By combining linear and bilinear interpolations and digital convolution filters to approximate bicubic interpolation, advantages such as quickly executed routine are possible. Generally, the algorithms use functions of linear interpolation and digital convolution filters, that are accelerated in OpenGL to approximate the bicubic interpolation. Linear, or bilinear, interpolation is a well defined function. Set forth below are the coefficients of convolution filters to be used in the algorithms.

More particularly, and in the first algorithm, two pass linear interpolation and 1 D filtering is utilized. The first pass performs interpolation in the x direction, and second pass repeats the same procedure for interpolation in the y direction. Interpolations in x and y directions are implemented using identical procedures, and both are performed in two steps. The linear interpolation is performed first, and then the 1 D convolution filter is applied to the interpolated data. The algorithm can be applied for any integer zoom factor n, and for any 1 D convolution filter size m.

To determine the coefficients of the 1 D convolution filter, the following procedure is used. The first step in the procedure is linear interpolation. The values of new pixels $\beta_i$, with respect to the pixel values of the source image 11, are given by the following equations:

$$B_i = \frac{(n-i+1)}{n} I_i + \frac{(i-1)}{n} I_2 \qquad (14)$$

for i=1, ... n (n odd), and $$B_i = \frac{(n-i+0.5)}{n} I_i + \frac{(i-0.5)}{n} I_2 \qquad (15)$$

for i=1, ... n (n even).

Using the linearly interpolated pixels $b_i$, (instances of Bj; i=1, 2, ... m) the m by 1 convolution filter is applied to obtain the output-pixel $O_k$. Therefore, the following expression for the output pixel $O_k$ is obtained:

$$O_i = \sum_{i=1}^{m} a_i b_i \qquad (16)$$

where $a_i$ (i=1, ... m), are the coefficients of the convolution filter. When the expressions for $b_i$ (i=1, ... m), or the values of corresponding $B_{op}$ from equations (1) or (2), are substituted in equation (3), the following expression is obtained:

$$O_i = \sum_{i_1=1}^{j} \sum_{i_2=1}^{m} k_{i_1 i_2} a_{i_2} I_{i_1} \qquad (17)$$

where $k_{ij}$ are the constant coefficients obtained by applying equations (14) or (17).

Using known expressions for bicubic interpolation, an alternate expression for the pixel value $O_k$ can be obtained:

$$O_k = \sum_{i=i}^{4} c_i I_i \qquad (18)$$

where $c_i$ are the coefficients derived from the expressions for cubic interpolation in the case of magnification by n. Comparing equations (17) and (18), and equating coefficients with corresponding input pixels values $i_j$, the set of up to four linear equations for the coefficients $a_m$ of the filter is obtained:

$$\sum_{i_2=1}^{m} k_{ii_2} a_{i_2} = c_i \qquad (19)$$

There can be less than four equations if the pixels obtained by bilinear interpolation used by the convolution filter do not have any contribution from some input pixels $i_j$. In that case, the number of equations is reduced by the number of such pixels.

The same procedure is repeated for the set of n consecutive output pixels $O_i$ (i=1, ... , n) that have different locations relative to the input pixels, and a system of linear equations for the convolution filter coefficients is obtained.

This system can be expressed in matrix form as:

$$C=KA \qquad (20)$$

where C is the vector of corresponding coefficients $c_i$ from right sides of equations (18), K is the matrix of coefficients $K_{ij}$ of those linear equations, and A is vector of m filter coefficients $a_i$, (i=1, ... , m). For practical values of zoom factors n and filter sizes m this represents an overdetermined system of linear equations. In this case, the solution is determined by using the linear least squares method, and it has the form:

$$A=(K^T K)^{-1} K^T C \qquad (21)$$

Upon determining the coefficients A of the convolution filter that is to be applied, the whole procedure for altering the spatial characteristics of a digital image is defined.

The second algorithm utilizes a two step procedure including bilinear interpolation followed by the application of a 2D convolution filter. The second algorithm can be applied for any integer magnification factor m, and for any 2D convolution filter size n.

As described above, the first step is bilinear interpolation. In the case of magnification by a factor n, there are $n^2$ pixels in the new, zoomed, image that have fundamentally different positions with respect to the pixels of the source image. The values of new pixels, $B_{ij}$, with respect to the pixel values of the source image, $I_{ij}$, are given by following equations:

$$B_{ij} = \frac{(n-i+1)(n-j+1)}{n^2} I_{11} + \frac{(n-i+l)(j-1)}{n^2} I_{12} + \frac{(i-1)(n-j+1)}{n^2} I_{21} + \frac{(i-1)(j-1)}{n^2} I_{22} \qquad (22)$$

for i,j=1, ... , n (n odd), and $$B_{ij} = \frac{(n-i+0.5)(n-j+0.5)}{n^2} I_{11} + \frac{(n-i+0.5)(j-0.5)}{n^2} I_{12} + \frac{(i-0.5)(n-j+0.5)}{n^2} I_{21} + \frac{(i-.05)(j-0.5)}{n^2} I_{22} \qquad (23)$$

for i, j=1, ... , n (n even). Values for $b_{ij}$ (instances of $B_{ij}$) can be calculated by using the expressions in equations (21) or (22) and substituting appropriate values for $I_{ij}$, i, and j depending on the position of $b_{ij}$ in the input image. Using the bilinear interpolated pixels $b_{ij}$ (ij=1, 2, ... , m) the m by m convolution filters applied to obtain the output pixels. The following expression for the output pixel $O_{ki}$ is obtained:

$$O_{ki} = \sum_{i=1}^{m} \sum_{j=1}^{m} a_{ij} b_{ij} \quad (24)$$

where $a_{ij}$ (i,j=1, . . . , m) are the coefficients of the convolution filter. If the expressions for $b_{ij}$, (i,j=1, . . . , m), or the values of the corresponding $B_{op}$ from equations (24) or (25), are substituted in equation (26), the following expressions are obtained:

$$O_{ki} = \sum_{i_1=1}^{j} \sum_{i_2=1}^{j} \sum_{i_3=1}^{m} \sum_{i_4=1}^{m} k_{i_1 i_2 i_3 i_4} a_{i_3 i_4} I_{i_1 i_2} \quad (25)$$

where a $k_{ijkl}$ are the constant coefficients obtained by applying equations (22) or (23).

Using known expressions for bicubic interpolation, the alternate expression for the pixel value $O_{ki}$ can be obtained:

$$O_{kl} = \sum_{i=1}^{4} \sum_{i=j}^{4} c_{ij} I_{ij} \quad (26)$$

where $c_{ij}$ are the coefficients derived from the expressions for bicubic interpolation in the case of magnification by n. Comparing equations (25) and (26), and equating coefficients with corresponding input pixel values Iij, a set of up to sixteen linear equations for the filter coefficients $a_{mn}$, is obtained:

$$\sum_{i_3=1}^{m} \sum_{i_4=1}^{m} k_{iji_3 i_4} a_{i_3 i_4} = c_{ij} \quad (27)$$

There can be less then sixteen equations if the pixels obtained by bilinear interpolation used by the convolution filter do not have any contribution from some input pixels $I_{ij}$. In that case, the number of equations is reduced by the number of such pixels. Repeating this procedure for all of the output pixels $O_{ij}$ (i,j=1, . . . , n) a system of linear equations for the convolution filter coefficients is obtained.

This system can be expressed in matrix form as:

$$C = KA \quad (28)$$

where C is the vector of the corresponding coefficients $c_{ij}$ from right sides of equations (14), K is the matrix of coefficients $k_{ijkl}$ of those linear equations, and A is the vector of filter coefficients $a_{ij}$, (i,j=1, . . . , m). For practical values of zoom factors n and filter sizes m this represents an overdetermined system of linear equations. In this case, the solution is obtained using the linear least squares method and it has the form:

$$A = (K^T K)^{-1} K^T C \quad (29)$$

Upon determining the coefficients A of the convolution filter that is to be applied, the whole procedure for altering the spatial characteristics of a digital image is defined.

The above described CT Fluoro system has an increased frame rate as compared to known fluoro system yet provides acceptable image quality. Of course, the system can implement only selected ones of the above described algorithms and a selected combination of such algorithms, and does not necessarily implement all the algorithms.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A computed tomography system comprising a display and configured to perform a fluoroscopy scan, said system also including a manual controller configured to manipulate images of a patient on said display during a fluoroscopy scan of the patient.

2. A computed tomography system in accordance with claim 1 wherein to manipulate images of a patient, said manual controller is configured to page displayed images forward and backwards, to save displayed images, to superimpose a grid on a displayed image, and to adjust preset window/levels, under manual operator control during a fluoroscopy scan.

3. A computed tomography system accordance with claim 1 further comprising a patient table and wherein said manual controller is further configured to manually control scan parameters and patient table motion.

4. A computed tomography system in accordance with claim 3 further comprising alignment lights configured to provide a scan plane reference on the patient, and wherein to manually control scan parameters, said manual controller is configured to manually initiate a gantry prep sequence and to manually control operation of said alignment lights.

5. A computed tomography system in accordance with claim 3 wherein to manually control patient table motion, said manual controller is configured to manually control table movement at a constant rate of speed, and to manually control table movement in preset distance increments.

6. A computed tomography system in accordance with claim 3 wherein to manually control patient table motion, said manual controller is configured to manually control movement of the patient table to a prescribed scan position, to manually control movement of the patient table at a constant speed, and to manually control latching and unlatching the patent table into a free-floating condition.

7. A computed tomography system configured to perform a fluoroscopy scan, said system also including a controller configured to selectively operate said system in a tap mode and in a continuous scan mode.

8. A computed tomography system in accordance with claim 7 wherein said controller comprises a foot pedal.

9. A computed tomography system in accordance with claim 7 further comprising an x-ray source and a display, and further configured to energize said x-ray source during said tap mode for a sufficient period of time to collect data for at least one image each time said controller is activated.

10. A computed tomography system in accordance with claim 7 further comprising an x-ray source, and further configured to de-energize said x-ray source within a predetermined period of time after deactuating said controller and after sufficient data has been collected to reconstruct a full image.

11. A computed tomography system comprising an x-ray source, an x-ray detector aligned with said x-ray source, a patient table configured to position a patient between said x-ray source and said x-ray detector, and a display configured to display images reconstructed from data acquired by said detector, said computed tomography system being configured to perform fluoroscopy scans of the patient, and further comprising a first manual controller configured to control scan parameters, motion of said patient table, and display of images on said display during a fluoroscopy scan of the patient, and a second manual controller configured to selectively control operation of said system in a tap mode and in a continuous scan mode.

12. A computed tomography system in accordance with claim 11 wherein to control display of images on said display, said first manual controller is configured to page displayed images forward and backwards, to save displayed images, to superimpose a grid on a displayed image, and to adjust preset window/levels, under manual operator control during a fluoroscopy scan.

13. A computed tomography system in accordance with claim 11 further comprising alignment lights configured to provide a scan plane reference on the patient, and wherein to manually control patient table motion and to control scan parameters, said first manual controller is configured to manually control table movement at a constant rate of speed, to manually control table movement in preset distance increments, and to manually control operation of said alignment lights.

14. A computed tomography system in accordance with claim 11 wherein to manually control patient table motion, said manual controller is configured to manually control table movement at a constant rate of speed, and to manually control table movement in preset distance increments.

15. A computed tomography system in accordance with claim 14 wherein to manually control patient table motions, said first controller is further configured to manually control movement of the patient table to a prescribed scan position, to manually control movement of the patient table at a constant speed, and to manually control latching and unlatching the patent table into a free-floating condition.

16. A computed tomography system in accordance with claim 11 wherein said second controller comprises at least one of a foot pedal, a hand switch, and a voice activated control.

17. A computed tomography system in accordance with claim 11 further configured to de-energize said x-ray source within a predetermined period of time after deactuating said second manually controller and after sufficient data has been collected to reconstruct a full image.

18. A computed tomography system in accordance with claim 11 further comprising alignment lights configured to provide a scan plane reference on the patient;

wherein to control scan parameters, motion of said patient table, and display of images on said display, said first manual controller is configured to manually initiate a gantry prep sequence, to manually control operation of said alignment lights, to manually control movement of the patient table to a prescribed scan position, to manually control movement of the patient table at a constant speed, to manually control latching and unlatching the patent table into a free-floating condition, to page displayed images forward and backwards, to save displayed images, to superimpose a grid on a displayed image, and to adjust preset window/levels, under manual operator control during a fluoroscopy scan.

19. A computed tomography system in accordance with claim 11 further comprising a gantry having mounted thereon said x-ray detector and said x-ray source, wherein said reconstructed images are three-dimensional images, said first controller comprises a track ball, and wherein said first controller is further configured to initiate an x-ray scan, to control view angle of a displayed three-dimensional image, to rock the displayed three-dimensional image back and forth at a predetermined speed, and to tilt the gantry.

20. A computed tomography system in accordance with claim 11 wherein said first manual controller is further configured to modify an image slice thickness during a procedure.

21. A computed tomograpy system in accordance with claim 11 further comprising a processor configured to perform image extrapolation to generate data for a fast image update.

* * * * *

UNITED STATES PATENT AND TRADEMARK OFFICE
CERTIFICATE OF CORRECTION

PATENT NO. : 6,801,594 B1
APPLICATION NO. : 08/979279
DATED : October 5, 2004
INVENTOR(S) : Ali et al.

It is certified that error appears in the above-identified patent and that said Letters Patent is hereby corrected as shown below:

Column 20, line 20, after "tomography system" insert -- in --.

Column 20, line 41, delete "patent" and insert therefor -- patient --.

Column 21, line 32, delete "patent" and insert therefor -- patient --.

Column 22, line 15, delete "patent" and insert therefor -- patient --.

Column 22, line 34, delete "tomograpy" and insert therefor -- tomography --.

Signed and Sealed this

Nineteenth Day of December, 2006

JON W. DUDAS
*Director of the United States Patent and Trademark Office*